United States Patent
Li et al.

(10) Patent No.: US 11,208,492 B2
(45) Date of Patent: Dec. 28, 2021

(54) ANTI-CD20 ANTIBODY

(71) Applicant: BEIJING MABWORKS BIOTECH CO. LTD., Beijing (CN)

(72) Inventors: Feng Li, Beijing (CN); Boyan Zhang, Foster City, CA (US); Pei Ye, Lawrenceville, GA (US)

(73) Assignee: BEIJING MABWORKS BIOTECH CO. LTD., Beijing (CN)

( * ) Notice: Subject to any disclaimer, the term of this patent is extended or adjusted under 35 U.S.C. 154(b) by 0 days.

(21) Appl. No.: 16/275,142

(22) Filed: Feb. 13, 2019

(65) Prior Publication Data

US 2019/0177423 A1 Jun. 13, 2019

Related U.S. Application Data

(63) Continuation of application No. PCT/CN2017/099287, filed on Aug. 28, 2017.

(51) Int. Cl.
| | |
|---|---|
| C07K 16/28 | (2006.01) |
| A61P 35/02 | (2006.01) |
| A61P 37/02 | (2006.01) |
| A61P 35/00 | (2006.01) |
| A61P 37/00 | (2006.01) |
| A61K 39/00 | (2006.01) |

(52) U.S. Cl.
CPC .......... *C07K 16/2887* (2013.01); *A61P 35/00* (2018.01); *A61P 35/02* (2018.01); *A61P 37/00* (2018.01); *A61P 37/02* (2018.01); *A61K 2039/505* (2013.01); *C07K 2317/14* (2013.01); *C07K 2317/24* (2013.01); *C07K 2317/41* (2013.01); *C07K 2317/72* (2013.01); *C07K 2317/732* (2013.01); *C07K 2317/734* (2013.01); *C07K 2317/90* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 9,539,251 | B2 | 1/2017 | Sampath et al. |
| 2014/0242080 | A1 | 8/2014 | Jaeger et al. |
| 2015/0210772 | A1 | 7/2015 | Kim |
| 2016/0145354 | A1 | 5/2016 | Bacac et al. |

FOREIGN PATENT DOCUMENTS

| | | |
|---|---|---|
| CN | 1693467 A | 11/2005 |
| CN | 104768581 A | 7/2015 |
| CN | 104936985 A | 9/2015 |
| CN | 105143270 A | 12/2015 |
| CN | 105899535 A | 8/2016 |
| CN | 107217042 A | 9/2017 |
| WO | 2013013013 A2 | 1/2013 |
| WO | 2013013013 A3 | 5/2014 |
| WO | 2014160490 A1 | 10/2014 |
| WO | 2015110923 A2 | 7/2015 |
| WO | 2016068799 A1 | 5/2016 |

OTHER PUBLICATIONS

Peiqing Zhang, et al., "CHO Glycosylation Mutants as Potential Host Cells to Produce Therapeutic Proteins with Enhanced Efficacy", Adv Biochem Eng Biotechnol (2013) 131:63-87, Nov. 10, 2012.

Chan, Kah Fai et al., "Inactivation of GDP-fucose transporter gene (Slc35c1) in CHO cells by ZFNs, TALENs and CRISPR-Cas9 for production of fucose-free antibodies", Biotechnology Journal, 2016, 11, 399-414.

Niederfellner, G. et al., "Chain L, Epitope Characterization And Crystal Structure Of Ga101 Provide Insights Into The Molecular Basis For The Type I Type II Distinction of Anti-Cd20 Antibodies", NCBI Genbank., Oct. 10, 2012, pp. 1-2.

Niederfellner, G. et al., "Epitope characterization and crystal structure of GA101 provide insights into the molecular basis for type I/II distinction of CD20 antibodies", BLOOD, vol. 118, No. 2, pp. 358-367, Jul. 14, 2011.

International Search Report dated Nov. 22, 2017 issued in PCT/CN2017/099287.

Fabian Higel, et al., "N-glycosylation heterogeneity and the influence on structure, function and pharmacokinetics of monoclonal antibodies and Fc fusion proteins", European Journal of Pharmaceutics and Biopharmaceutics, Elsevier Science Publishers B.V., vol. 100, Jan. 13, 2016, pp. 94-100.

Takahiro Ishiguro, et al., "A defucosylated anti-CD317 antibody exhibited enhanced antibody-dependent cellular cytotoxicity against primary myeloma cells in the presence of effectors from patients", Cancer Science, vol. 101, No. 10, pp. 2227-2233, Aug. 5, 2010.

Liming Liu, "Antibody Glycosylation and Its Impacton the Pharmacokinetics and Pharmacodynamics of Monoclonal Antibodies and Fc-Fusion Proteins", Journal of Pharmaceutical Sciences, vol. 104, No. 6, pp. 1866-1884, Jun. 1, 2015.

(Continued)

*Primary Examiner* — Sharon X Wen
(74) *Attorney, Agent, or Firm* — Perkins Coie LLP; Viola T. Kung

(57) ABSTRACT

The present invention relates to a humanized anti-CD20 antibody that comprises an antigen binding site containing heavy and light chain of obinutuzumab (GAZYVA®), and N-linked oligosaccharides that are attached to the Fc region of the antibody, wherein the N-linked oligosaccharides are not bisected by N-acetylglucosamine. The antibody of the present invention comprises fucose glycotype in an amount of no more than 10% of the total N-glycans that are attached to the Fc region of the antibody. The anti-CD20 of the present invention has antibody dependent cell-mediated cytotoxicity (ADCC) about 2 times stronger than that of GAZYVA® and about 50 to 100 times stronger than that of RITUXAN®. The anti-CD20 antibodies are effective for treating CD20 expressing cancer, such as non-Hodgkin's lymphoma, B cell lymphoma, chronic lymphocytic leukemia, or follicular lymphoma.

2 Claims, 8 Drawing Sheets

Specification includes a Sequence Listing.

(56) References Cited

OTHER PUBLICATIONS

Ekkehard Mössner, et al., "Increasing the efficacy of CD20 antibody therapy through the engineering of a new type II anti-CD20 antibody with enhanced direct and immune effector cell-mediated B-cell cytotoxicity", Blood, vol. 115, No. 22, pp. 4393-4402, Jun. 3, 2010.

Dietmar Reusch, et al., "Fc glycans of therapeutic antibodies as critical quality attributes", Glycobiology, vol. 25, No. 12, pp. 1325-1334, Aug. 11, 2015.

Robert L. Shields, et al., "Lack of Fucose on Human IgG1 N-Linked Oligosaccharide Improves Binding to Human FcyRIII and Antibody-dependent Cellular Toxicity", Journal of Biological Chemistry, American Society for Biochemistry and Molecular Biology, vol. 277, No. 30, pp. 26733-26740, Jul. 26, 2002.

Supplementary European Search Report dated Mar. 6, 2020 cited in EP 17845369.

SEQUENCE LISTING

<160> NUMBER OF SEQ ID NOS: 4

<210> SEQ ID NO 1
<211> LENGTH: 219
<212> TYPE: PRT
<213> ORGANISM: Homo sapiens

<400> SEQUENCE: 1

Asp Ile Val Met Thr Gln Thr Pro Leu Ser Leu Pro Val Thr Pro Gly
1               5                   10                  15

Glu Pro Ala Ser Ile Ser Cys Arg Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 2
<211> LENGTH: 449
<212> TYPE: PRT
<213> ORGANISM: Homo sapiens

<400> SEQUENCE: 2

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Tyr Ser
                 20                  25                  30

Trp Ile Asn Trp Val Arg Gln Ala Pro Gly Gln Gly Leu Glu Trp Met
             35                  40                  45

Gly Arg Ile Phe Pro Gly Asp Gly Asp Thr Asp Tyr Asn Gly Lys Phe
         50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
```

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 3
<211> LENGTH: 657
<212> TYPE: DNA
<213> ORGANISM: Homo sapiens

<400> SEQUENCE: 3
gatatcgtga tgacccagac tccactctcc ctgcccgtca cccctggaga gcccgccagc    60
attagctgca ggtctagcaa gagcctcttg cacagcaatg gcatcactta tttgtattgg   120
tacctgcaaa agccagggca gtctccacag ctcctgattt atcaaatgtc caaccttgtc   180
tctggcgtcc ctgaccggtt ctccggatcc gggtcaggca ctgatttcac actgaaaatc   240
agcagggtgg aggctgagga tgttggagtt tattactgcg ctcagaatct agaacttcct   300
tacaccttcg gcgagggac caaggtggag atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt     657

<210> SEQ ID NO 4
<211> LENGTH: 1347

<212> TYPE: DNA
<213> ORGANISM: Homo sapiens

<400> SEQUENCE: 4

```
caggtgcaat tggtgcagtc tggcgctgaa gttaagaagc ctgggagttc agtgaaggtc      60
tcctgcaagg cttccggata cgccttcagc tattcttgga tcaattgggt gcggcaggcg     120
cctggacaag ggctcgagtg gatgggacgg atctttcccg gcgatgggga tactgactac     180
aatgggaaat tcaagggcag agtcacaatt accgccgaca aatccactag cacagcctat     240
atggagctga gcagcctgag atctgaggac acggccgtgt attactgtgc aagaaatgtc     300
tttgatggtt actggcttgt ttactgggc cagggaaccc tggtcaccgt ctcctcagct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgactgtg ccctctagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                         1347
```

ANTI-CD20 ANTIBODY

This application is a continuation of PCT/CN2017/099287, filed Aug. 28, 2017; which claims the priority of CN201610791273.1, filed Aug. 31, 2016. The contents of the above-identified applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Oct. 1, 2018, and a size of 8.69 kilobytes. The Sequence Listing filed via EFS-Web is part of the specification and is hereby incorporated in its entirety by reference herein.

TECHNICAL FIELD

The present invention relates to an anti-human CD20 humanized monoclonal antibody; the antibody does not comprise bisected N-glycan and comprises fucose glycotype in an amount of no more than 10% of the total saccharides that are attached to the Fc region of the antibody. The present invention also relates to the use of the humanized monoclonal antibody for treating tumors, autoimmune diseases and inflammations.

BACKGROUND OF THE INVENTION

Leukocyte differentiation antigen (cluster of differentiation, CD) refers to the cell surface markers of the blood cells in the process of differentiation and maturation. CD20 is a molecule present on the B lymph cell surface and expression thereof is seen in normal B cells in peripheral blood, spleen, tonsil and bone marrow and so forth as well as B cells in most of malignant tumors. CD20 may function on B cells directly by way of regulating transmembrane calcium ion flow; it may also play an important regulatory role in B cell proliferation and differentiation. CD20 antigen is a B cell differentiation antigen, which is only present in the pre-B cells and mature B cells. CD20 is expressed in more than 95% of B cell lymphoma, while it is not expressed in hematopoietic stem cells, plasma cells and other normal tissues. CD20 molecule comprises 297 amino acid residues, penetrates a cell membrane four times, and has both the C-terminus and N-terminus inside the cell, and has the only extracellularly exposed loop with no sugar chain consisting of 43 amino acid residues between the third and fourth transmembrane domains.

Rituximab (RITUXAN®) antibody is a genetically engineered chimeric human gamma 1 murine constant domain containing monoclonal antibody directed against the human CD20 antigen. This chimeric antibody contains human gamma 1 constant domains and is identified by the name "C2B8" in U.S. Pat. No. 5,736,137. RITUXAN® is approved for the treatment of patients with relapsed or refracting low-grade or follicular, CD20 positive, B cell non-Hodgkin's lymphoma. In vitro mechanism of action studies have shown that RITUXAN® exhibits human complement-dependent cytotoxicity (CDC) (Reff et al, Blood 83(2): 435-445 (1994)). Additionally, it exhibits significant activity in assays that measure antibody-dependent cellular cytotoxicity (ADCC).

Obinutuzumab (called afutuzumab until 2009, originally GA101) is a humanized anti-CD20 monoclonal antibody, originated by GlycArt Biotechnology AG and developed by Roche as a cancer treatment. It was approved under the trade name GAZYVA® by the US FDA in 2013, for the treatment of chronic lymphocytic leukemia in combination with chemotherapy in treatment-naive patients, and as a second line treatment for follicular lymphoma. GAZYVA® is produced by a mutant CHO cell that overexpresses β(1,4)-N-acetyl-glucosaminyltransferase III (GnTIII), a glycosyltransferase catalyzing the formation of bisected oligosaccharides (U.S. Pat. No. 9,296,820).

Monoclonal antibodies undergo glycosylation in the ER and Golgi network of cells. The glycan structures of therapeutic monoclonal antibodies can be of importance for the efficacy and safety of the drug. Monoclonal antibodies have one conserved N-linked glycosylation at the Fc part at position N297. Approximately 20% monoclonal antibodies contain a second N-linked glycosylation site in their variable region. Both glycosylation sites are located on the heavy chain. Glycosylation of biopharmaceuticals shows a high grade of heterogeneity and N-glycans belong to the most complex and diverse structures in nature due to the high number of different sugar moieties and the multitude of possible linkages. See Higel et al (*European J. Pharmaceutics and Biopharmaceutics* 100: 94-100, 2016).

At present, there is a need for developing new anti-CD20 antibodies with improved activities.

DETAILED DESCRIPTION OF THE INVENTION

Definitions

Figure 1:
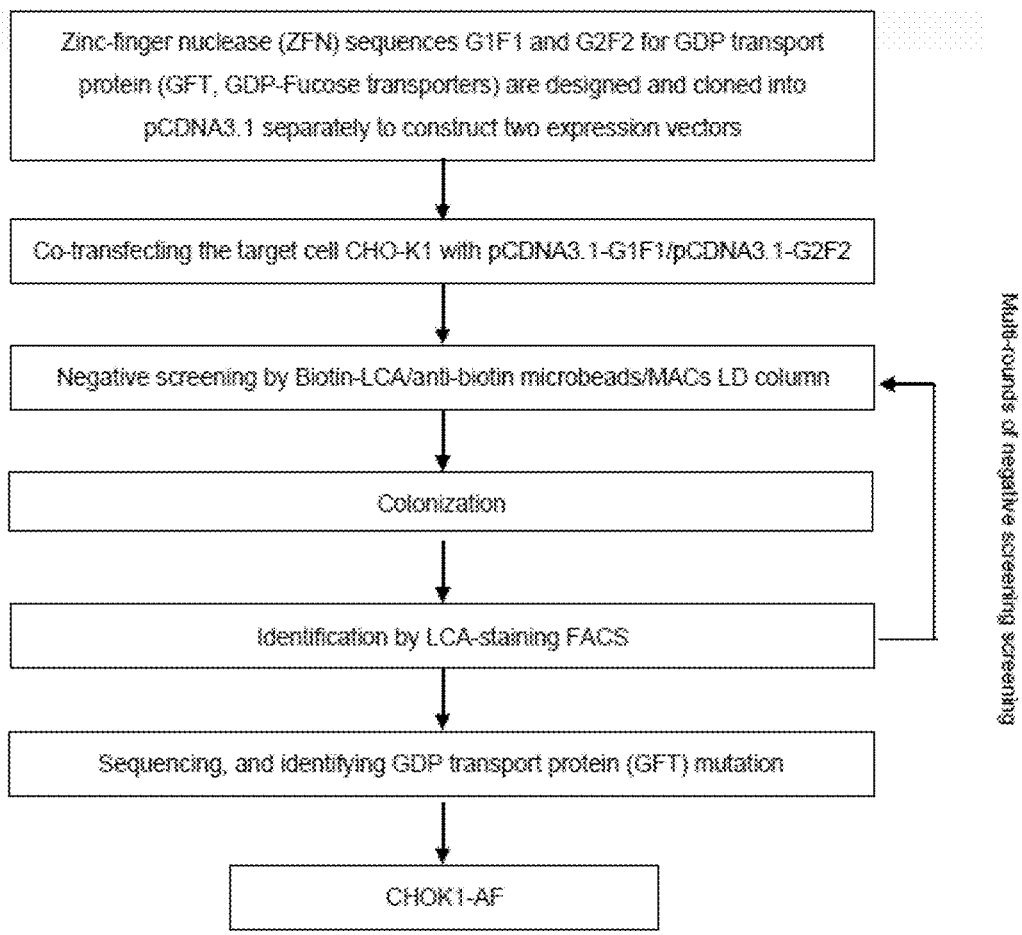
FIG. 1 shows a flow chart of the method for preparing a CHO mutant CHOK1-AF, in which the Slc35c1 gene is knocked out.

As used herein, the term "about" refers to ±10% of the recited value.

As used herein, the term "an effective amount" refers to an amount to obtain or at least partially obtain a desired effect. An effective amount can be determined by a skilled technician in the art. For example, an effective amount for treatment use depends on severity of disease to be treated, general status of immune system of a patient, general status of a patient such as age, body weight and gender, administration method for drugs, and other therapies simultaneously applied.

As used herein, the term "adjuvant" refers to a non-specific immune enhancer, when it is delivered with an antigen, it can enhance immune response of a subject to the antigen or change type of immune response. There are many kinds of adjuvants, including but not being limited to aluminum adjuvants (e.g., aluminum hydroxide), Freund's adjuvants, lipopolysaccharides, and cell factors. Freund's adjuvants are the most popular adjuvants in animal tests at present, while aluminum hydroxide adjuvant is often used in clinical experiments.

As used herein, the term "antibody" refers to an immune globulin usually consisting of two pairs of polypeptide chains (each pair has a light (L) chain and a heavy (H) chain). The antibody light chain can be classified as κ light chain and λ light chain. The heavy chain can be classified as μ, δ, γ, α or ε, and isotypes of antibody are separately defined as IgM, IgD, IgG, IgA and IgE. In light chain and heavy chain, variable region and constant region are linked via "J" region with about 12 or more amino acids, and heavy chain further contains "D" region with about 3 or more amino acids. Each heavy chain consists of a heavy chain variable region ($V_H$) and heavy constant region ($C_H$). Heavy chain consists of 3 domains (CH1, CH2, and CH3). Each light chain consists of a light chain variable region ($V_L$) and a light chain constant region ($C_L$). The constant regions of antibody can mediate immune globulin to bind to host tissues or factors, including various cells (e.g., effector cells) of immune system and first component (C1q) of classical complement system. $V_H$ and $V_L$ regions can further be classified as high variability regions (called as complementary determining region (CDR)), in which relatively conservative regions called as framework regions (FR) are scattered. These $V_H$ and $V_L$ regions are composed of 3 CDR regions and 4 FR regions in order of: FR1, CDR1, FR2, CDR2, FR3, CDR3, FR4, from amino terminal to carboxyl terminal. Variable regions ($V_H$ and $V_L$) of each pair of heavy chain/light chain form an antibody binding site.

As used herein, "antibody-dependent cell-mediated cytotoxicity" (ADCC) is a mechanism of cell-mediated immune defense whereby an effector cell of the immune system actively lyses a target cell, whose membrane-surface antigens have been bound by specific antibodies.

As used herein, the term "antigen-binding fragment" of antibody refers to a polypeptide containing a fragment of full-length antibody, which remains ability of specifically binding to the same antigen to which the full-length antibody binds, and/or competes with the full-length antibody to specifically bind to antigen.

As used herein, "bisecting N-acetylglucosamine (GlcNAc)" is a β1-4-linked GlcNAc residue attached to a β-mannose of the N-glycan core, and the reaction is catalyzed by N-acetylglucosaminyltransferase-III (GnT-III/Mgat-III). Reports have suggested that sugar chains containing bisecting GlcNAc are involved in a variety of biological functions such as cell-cell and cell-matrix interactions, cell growth control, and tumor progression (Nagae et al, *J. Biol. Chem.* 288:33598-33610, 2013).

As used herein, the term "complement-dependent cytotoxicity" (CDC) is a function of the complement system. It is the processes in the immune system that kill pathogens by damaging their membranes without the involvement of antibodies or cells of the immune system.

As used herein, the term "core fucose" refers to a fucose linked to GlcNAc in connection with asparagine in N-glycan core pentasaccharides.

As used herein, the term "EC50" refers to concentration for 50% of maximal effect, that is, a concentration that causes 50% of maximal effect.

As used herein, the term "FcγRIIIa" is a 50-70 kDa glycoprotein, belonging to Ig superfamily, having two C2 structures, and its gene is located at 1q23-24 of chromosome. FcγRIII binds to human IgG, IgG3, and is a low affinity receptor. FcγRIII comprises 2 allotypes, FcγRIII A and FcγRIII B. FcγRIII A (AAH17865.1, GenBank) has a transmembrane structure and is mainly distributed in macrophages, NK cells and eosinophilic granulocytes, in which macrophages have a high expression level of FcγRIII A, while mononuclear cells have a lower expression level. FcγRIII A relates to disulfide bond-linked CD3ζ or FcεR I γ chain dimer, in which FcγRIII A relates to CD3 complex γ chain on macrophages, while FcγR III A relates to ζ chain on NK/LGL.

As used herein, the term "FcRn" is neonate Fc receptor (P61769, UniProtKB/Swiss-Prot), which is a heterologous dimer consisting of a large subunit and a small subunit, the large subunit has a molecular weight of 45-53 kD, called as α chain; the small subunit is β2 microglobulin (β2m), has a molecular weight of 14 kD, called as β chain, the two chains are bound together in a non-covalent bond form. When physiologic pH is 7.4, FcRn does not bind to IgG, but under condition of endosome acidic pH 6-6.5, affinity of FcRn to IgG Fc ranges from nanomoles to micromoles.

As used herein, the term "host cell" refers to a cell into which a vector can be introduced, which includes but is not limited to, for example, prokaryotic cells such as *E. coli* or *Bacterium subtilis*, fungus cells such as yeast cells or *Aspergillus*, insect cells such as S2 fruit fly cells or Sf9 cells, or animal cells such as fibroblasts, CHO cells, COS cells, NSO cells, Hela cells, BHK cells, HEK293 cells or human cells.

As used herein, the term "humanized" generally refers to a process of making an antibody or immunoglobulin binding proteins and polypeptides derived from a non-human species (e.g., mouse or rat) to be less immunogenic to humans, while still retaining antigen-binding properties of the original antibody, using genetic engineering techniques. In some embodiments, the binding domain(s) of an antibody or an immunoglobulin binding protein or polypeptide (e.g., light and heavy chain variable regions, Fab, scFv) are humanized. Non-human binding domains can be humanized using techniques known as CDR grafting, including reshaping, hyperchimerization, and veneering. If derived from a non-human source, other regions of the antibody or immunoglobulin binding proteins and polypeptides, such as the hinge region and constant region domains, can also be humanized.

As used herein, the term "$K_D$" refers to a dissociation equilibrium constant for a specific antibody-antigen interaction, which is used to describe binding affinity between the antibody and the antigen.

As used herein, the term "pharmaceutically acceptable carrier and/or excipient" refers to a carrier and/or excipient pharmacologically and/or physiologically compatible to a subject and an active component, for example, see Remington's Pharmaceutical Sciences. Edited by Gennaro A R, 19th ed. Pennsylvania: Mack Publishing Company, 1995. A pharmaceutically acceptable carrier includes but is not limited to: pH regulators, surfactants, adjuvants, ion strength enhancers. For example, pH regulators include but are not limited to phosphate buffer solutions; surfactants include but are not limited to cationic, anionic or nonionic surfactants, for example, Tween-80; ion strength enhancers include but are not limited to sodium chloride.

As used herein, the term "specifically binding" refers to a non-random binding reaction between two molecules, for example, a reaction between an antibody and its antigen.

As used herein, the term "vector" refers to a nucleic acid vector that can be used for inserting polynucleotide. When a vector enables an inserted polynucleotide to express a protein encoded thereby, the vector is called as expression vector. Vector can be introduced into a host cell by transformation, transduction or transfection, so that a genetic material element carried by the vector is expressed in the host cell. Vectors are well-known by those skilled in the art, including but not being limited to: plasmids, phasmids, cosmids, artificial chromosomes, for example, yeast artificial chromosomes (YAC), bacterial artificial chromosomes (BAC) or P1-sourced artificial chromosomes (PAC); phages such as λ phages or M13 phages and animal viruses. The animal viruses usable as vectors include but are not limited to retroviruses (including lentiviruses), adenoviruses, adeno-associated viruses, herpes viruses (e.g., herpes simplex virus), poxviruses, baculoviruses, papillomaviruses, papovaviruses (e.g., SV40). A vector can contain a plurality of expression-controlling elements, including but not being limited to promoter sequence, transcription initiation sequence, enhancer sequences, selection element and reporter gene. In addition, vector may further contain replication initiation site.

DESCRIPTION

The present disclosure provides a humanized anti-CD20 antibody that has an altered and improved pattern of glycosylation in its Fc region. The anti-CD20 antibody of the present invention has an increased ADCC (antibody-dependent cell-mediated cytotoxicity) activity and reduced CDC (complement-dependent cytotoxicity) activity, as a result of the improved pattern of glycosylation in the Fc region.

The present invention provides a humanized anti-CD20 antibody that comprises an antigen binding site containing heavy and light chains of GAZYVA® (obinutuzumab), and N-linked oligosaccharides that are attached to the Fc region of the antibody. The humanized anti-CD20 antibody of the present invention is produced by a mutant CHO cell that has a dysfunctional Slc35C1 gene that regulate glycosylation. Contrary to GAZYVA®, the N-linked oligosaccharides in the present antibody are not bisected by N-acetylglucosamine. Contrary to GAZYVA®, the present antibody contains a very low amount of core fucose. The antibody of the present invention in general comprises fucose glycotype in an amount of no more than 10% of the total N-glycans that are attached to the Fc region of the antibody. The anti-CD20 of the present invention has antibody dependent cell-mediated cytotoxicity (ADCC) about 2 times stronger than that of GAZYVA® and about 50 to 100 times stronger than that of RITUXAN®.

The present invention is directed to a humanized anti-CD20 antibody or an antigen binding fragment thereof, comprising an antigen binding site containing a heavy chain and a light chain of GAZYVA®, and N-linked oligosaccharides that are attached to the Fc region of the antibody, wherein the N-linked oligosaccharides are not bisected by N-acetylglucosamine.

In one embodiment, the light chain amino acid sequence of the anti-CD20 antibody of the present invention is shown as follows, or a sequence having at least 95%, or at least 97%, or at least 99% identity:

(SEQ ID NO: 1)
DIVMTQTPLSLPVTPGEPASISCRSSKSLLHSNGITYLYWYLQKPGQSPQ

LLIYQMSNLVSGVPDRFSGSGSGTDFTLKISRVEAEDVGVYYCAQNLELP

YTFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

The heavy chain amino acid sequence of the anti-CD20 antibody of the present invention is shown as follows, or a sequence having at least 95%, or at least 97%, or at least 99% identity:

(SEQ ID NO: 2)
QVQLVQSGAEVKKPGSSVKVSCKASGYAFSYSWINTWVRQAPGQGLEWM

GRIFPGDGDTDYNGKFKGRVTITADKSTSTAYMELSSLRSEDTAVYYCA

RNVFDGYWLVYWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK, in which the underlined sequence is the variable region sequence thereof.

In one embodiment, the nucleotide sequence of for encoding the light chain of the anti-CD20 is as follows, or a sequence having at least 95%, or at least 97%, or at least 99% identity:

Gatatcgtgatgacccagactccactctccctgcccgtcaccctg-gagagcccgccagcattagctgcaggtctagcaagag
cctcttgcacagcaatggcatcacttatttgtat-tggtacctgcaaaagccagggcagtctccacagctcctgatttatcaaatgtc-caaccttgt ctctggcgtccctgaccggttctccggatccgggtcaggcactgat-ttcacactgaaaatcagcagggtggaggctgaggatgttggagttt
attactgcgctcagaatctagaacttccttacaccttcggcggagggaccaaggtg-gagatcaaacgtacggtggctgcaccatctgtcttca tcttcccgccatctgat-gagcagttgaaatctggaactgcctctgttgtgtgcctgctgaataacttc-tatcccagagaggccaaagtacagtg
gaaggtggataacgccctccaatcgggtaactcccaggagagtgt-cacagagcaggacagcaaggacagcacctacagcctcagcagc
accctgacgctgagcaaagcagactacgagaaacacaaagtc-tacgcctgcgaagtcacccatcagggcctgagctcgcccgtcacaaa gagctt-caacaggggagagtgt (SEQ ID NO: 3), in which the underlined sequence is the variable region sequence thereof.

In one embodiment, the nucleotide sequence of for encoding the heavy chain of the anti-CD20 is as follows, or a sequence having at least 95%, or at least 97%, or at least 99% identity:

caggtgcaattggtgcagtctggcgctgaagttaagaagcctggagttcagt-gaaggtctcctgcaaggcttccggatacgcct tcagctattcttggatcaat-tgggtgcggcaggcgcctggacaagggctcgagtggatgggacg-gatctttcccggcgatggggatactga
ctacaatgggaaattcaagggcagagtcacaattaccgccgacaaatccactagcacagcctatatggagctgagcagcctgagatctgag
gacacggccgtgtattactgtgcaagaaatgtctttgatggttactggcttgtt-
tactggggccagggaaccctggtcaccgtctcctcagcta gcaccaagggcc-
catcggtcttcccctggcaccctcctc-
caagagcacctctgggggcacagcggccctgggctgcctggtcaaggac
tacttccccgaaccggtgacggtgtcgtg-
gaactcaggcgccctgaccagcggcgtgcacaccttcccggctgtccta-
cagtcctcaggac
tctactccctcagcagcgtggtgactgtgccctctagcagcttgggcacccagacc-
tacatctgcaacgtgaatcacaagcccagcaacac caaggtggacaagaaagtt-
gagcccaaatcttgtgacaaaactcacacatgcccaccgtgcccagcacct-
gaactcctgggggaccgtc
agtcttcctcttccccccaaaacccaaggacaccctcatgatctcccgacccct-
gaggtcacatgcgtggtggtggacgtgagccacgaa gaccctgaggtcaagtt-
caactggtacgtggacggcgtggaggtgcataatgccaagacaaagccgcgg-
gaggagcagtacaacagca
cgtaccgtgtggtcagcgtcctcaccgtcctgcaccaggactggct-
gaatggcaaggagtacaagtgcaaggtctccaacaaagccctcc cagcccc-
catcgagaaaaccatctccaaagccaaagggcagccccgagaac-
cacaggtgtacaccctgcccccatcccgggatgagct
gaccaagaaccaggtcagcctgacctgcctggtcaaaggcttctatcccagcga-
catcgccgtggagtgggagagcaatgggcagccgg agaacaactacaagac-
cacgcctcccgtgctggactccgacggctccttcttcctctacagcaagct-
caccgtggacaagagcaggtggc
agcaggggaacgtcttctcatgctccgtgatgcatgaggctctgcacaaccacta-
cacgcagaagagcctctccctgtctccgggtaaa, (SEQ ID NO: 4), in
which the underlined sequence is the variable region
sequence thereof.

In one embodiment, the present invention relates to isolated nucleic acid molecules which are capable of encoding the light chain and the heavy chain of the anti-CD20 antibody of the present invention.

The oligosaccharide component of a glycoprotein such as an antibody can significantly affect properties relevant to therapeutic efficacy, including physical stability, resistance to protease attack, interactions with the immune system, pharmacokinetics, and specific biological activity. Such properties depend not only on the presence or absence, but also on the specific structures, of the oligosaccharides.

In one embodiment of the present invention, the anti-CD20 antibody or an antigen binding fragment thereof has a small amount of core fucose or lacks core fucose from the Fc N-glycans. For example, the anti-CD20 antibody or an antigen binding fragment thereof, contains fucose glycotype ≤25%, ≤20%, ≤15%, ≤10%, ≤8%, ≤6%, ≤5%, ≤4%, ≤3%, ≤2%, ≤1.5%, or ≤1.1% of the total N-glycans that are attached to the Fc region of the antibody. In a preferred embodiment, the ratio of glycotypes without core fucose is ≥98.5%, i.e., the glycotypes with core fucose is <1.5%. The content of fucose glycotype is obtained by summing contents of all fucose-containing glycotypes, e.g., determined by N-oligosaccharide determination method.

Figure 3:
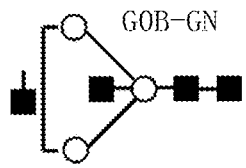
FIG. 3 shows structures of the N-Glycans that were enzymatically released from MIL62 and GAZYVA®.
Figure 3:
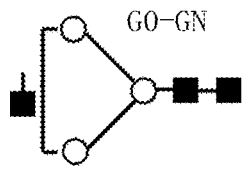
Figure 3:
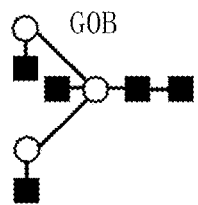
Figure 3:
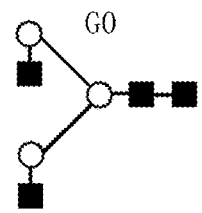
Figure 3:
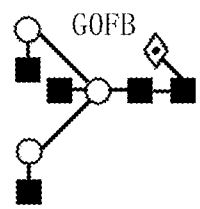
Figure 3:
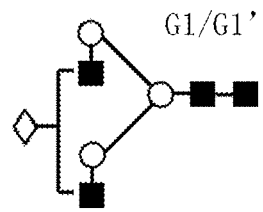
Figure 3:
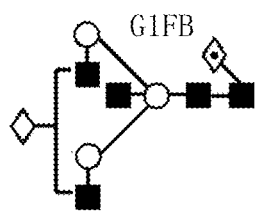
Figure 3:
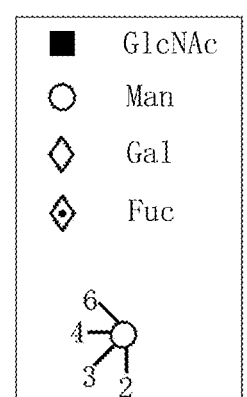
Figure 3:
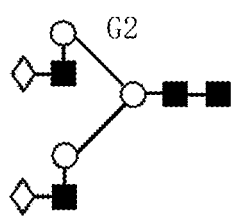

In another embodiment of the present invention, the anti-CD20 antibody or an antigen binding fragment thereof comprises N-linked oligosaccharides that are attached to the Fc region of the antibody, wherein the N-linked oligosaccharides do not contain a bisecting N-acetylglucosamine (GlcNAc), and the N-linked oligosaccharides are not bisected by N-acetylglucosamine. A common core structure of N-glycans are shown in FIG. 3, G0, which includes the first two GlcNAc residues, three mannose residues, and then two GlcNAc residues. FIG. 3 also shows bisected (B)N-glycan, where a bisecting GlcNAc is attached to the middle mannose of the N-glycan core and bisects the N-glycan. The main oligosaccharides of the anti-CD20 antibody of the present invention are not bisected by a bisecting N-acetylglucosamine (GlcNAc); whereas the main oligosaccharides of GAZYVA® contains about 77% of bisected oligosaccharides (see Example 6).

The anti-CD20 antibody of the present invention exhibits strong ADCC at low concentrations. This is because afucosylated antibody enhances its binding affinity with the Fc gamma receptor IIIa (FcγRIIIa) on the natural killer (NK) cells, and hence increases the antibody's ADCC activity. At the same time, afucosylated antibody can suppress the inhibitory effect from human immunoglobulin G (IgG) in serum for binding to the Fc gamma receptor IIIa (FcγRIIIa) on the natural killer (NK) and macrophage cells as the latter's binding affinity with FcγRIIIa is much weaker.

Removal of the core fucosylation to increase the antibody affinity with FcγRIIIa is one of the most effective ways to increase ADCC. Most therapeutic antibodies currently on the market are heavily fucosylated because they are produced by mammalian cell lines such as Chinese Hamster ovary (CHO) with intrinsic enzyme activity responsible for the core-fucosylation of the Fc N-glycans of the products. The present invention provides a CHO mutant that has a dysfunctional Slc35C1 gene, which encodes the GDP-fucose transporter SLC35C1 that critically regulates the fucosylation of glycans. The CHO mutant of the present invention only contains one dysfunctional gene from CHO that affects the regulation of glycan, i.e., the Slc35C1 gene is knocked out; the CHO mutant does not contain any other dysfunctional gene that affects the regulation of glycans. For example, the CHO mutant does not contain a dysfunctional gene that affects the production of sialic acids. The SLC35C1-deficient CHO cells produce antibody with fucose-containing glycotype content about ≤10%, ≤8%, ≤6%, ≤4%, ≤3%, ≤2%, ≤1.5%, or ≤1.1% of the total oligosaccharides that are attached to the Fc region of the antibody.

The present invention provides a method to produce mutant SLC35C1-deficient CHO cells, which are capable of producing antibody with a low level of core fucose. CHO cells produce glycosylated proteins and provide consistent generation of genetically stable, highly productive clonal cell lines. CHO cells can be cultured to high densities in simple bioreactors using serum-free media, and permit the development of safe and reproducible bioprocesses.

The mutant SLC35C1-deficient CHO cells are prepared by using the zinc finger enzyme knock-out technique to knock out the key fucose-modified protein GFT (GDP-fucose transporter) in the host CHO cells, and thus the fucosylated level of the antibody produced is effectively reduced. This method can block both the classical and the compensatory pathways of fucosylation, so the method is effective in reducing fucosylation. The method comprises using zinc-finger nuclease technique to design two GFT zinc-finger nucleases for GFT gene Slc35c1 sequence (Gen-Bank: BAE16173.1); the two zinc-finger nucleases are designed to bind double-stranded DNA of the target gene separately. The two zinc-finger nuclease sequences for GFT are cloned to construct two expression vectors. The two expression vectors are co-transfected into the target CHO cells by a suitable method known to a skilled person, e.g., by electrotransfection technique. After transfection, the transfected cells are cultivated, performed passage and amplification. The clones without fucosylation modification are selected via multi-turns of negative separation and clonal culture. One specific method is illustrated in FIG. 1.

The present invention provides a method to remove the core fucosylation of the antibody, which improves the ADCC effect of the antibody. In the present method, the antibody is produced using a CHO mutant that has a dysfunctional Slc35C1 gene, which results in the core-fucose glycotype level of less than 1.5% of the total N-glycans. For comparison, GAZYVA® has bisected N-Glycan and has a high level (48%) of core fucose (see Example 6). As a result, the anti-CD20 of the present invention has about 2-fold increase in ADCC activity compared to GAZYVA® (see Example 12).

In one aspect, the present invention provides a host cell, which is a Chinese Hamster ovary (CHO) mutant cell line comprising a dysfunctional Slc35C1 gene, and a vector comprising polynucleotides encoding the amino acid sequences of a light chain and a heavy chain of a humanized anti-CD20 antibody, for example, SEQ ID NOs. 1 and 2. In one embodiment, the CHO mutant cells only contain one dysfunctional gene that affects the regulations of glycan. In one embodiment, the polynucleotides encoding SEQ ID NOs. 1 and 2 have the nucleic acid sequences of SEQ ID NOs. 3 and 4, respectively. Preferably, in the host cell, the gene of GFT (key protein in fucose modification pathway) is site-directly knocked out. Preferably, the knockout is performed by zinc finger nuclease technique. Preferably, the SLC35c1 sequence in the gene of GFT (GenBank accession number: BAE16173.1) is site-directly knocked out.

In another aspect, the present invention provides a conjugate, which comprises an anti-CD20 antibody or an antigen binding fragment thereof and a coupling part. For example, the coupling part is a detectable label such as a radioactive isotope, a fluorescent material, a luminescent material, a colored material or an enzyme.

In another aspect, the present invention provides a kit, which comprises the anti-CD20 antibody or an antigen binding fragment thereof according to the present invention, or comprises the conjugate of the present invention. The kit may further comprise a second antibody, which specifically recognizes the anti-CD20 antibody or an antigen binding fragment thereof; optionally, the second antibody further comprises a detectable label, such as a radioactive isotope, a fluorescent material, a luminescent material, a colored material or an enzyme.

In another aspect, the present invention relates to a use of the anti-CD20 antibody or an antigen binding fragment thereof according to the present invention or the conjugate of the present invention in manufacturing a kit, wherein the kit is used for detecting the existence of CD20 or the level of CD20 in a sample.

In another aspect, the present invention relates to a pharmaceutical composition, which comprises the anti-CD20 antibody or an antigen binding fragment thereof or the conjugate of the present invention; optionally, further comprises a pharmaceutically acceptable carrier and/or an excipient; optionally, further comprises one or more chemotherapeutic drugs or cytotoxic drugs. The chemotherapeutic drug or cytotoxic drug may be selected from: (1) drugs acting on DNA chemical structure: alkylating agent such as mechlorethamines, nitroso urines, methylsulfonic acid esters; platinum compounds such as cis-platinum, carboplatin and oxaliplatin, etc.; mitomycin (MMC); (2) drugs affecting synthesis of nucleic acids: dihydrofolate reductase inhibitors such as methotrexate (MTX) and Alimta, etc.; thymidine synthase inhibitor such as fluorouracils (5FU, FT-207, capecitabine), etc.; purine nucleoside synthase inhibitors such as 6-mercaptopurine (6-MP) and 6-TG, etc.; nucleotide reductase inhibitors such as hydroxyurea (HU), etc.; DNA polymerase inhibitors such as cytarabine (Ara-C) and Gemz, etc.; (3) drugs acting on nucleic acid transcription: drugs for inhibiting RNA synthesis by selectively acting on DNA templates, inhibiting DNA-dependent RNA polymerase, such as: actinomycin D, rubidomycin, adriamycin, epirubicin, aclacinomycin, mithramycin, etc.; (4) drugs mainly acting on microtubulin synthesis: paclitaxel, docetaxel, vinblastinum, vinorelbine, podophyllotoxins, homoharringtonine; (5) other cytotoxic drugs: asparaginase mainly inhibiting protein synthesis; hormones: antiestrogens: tamoxifen, droloxifen, exemestane, etc.; aromatase inhibitors: aminoglutethimide, lentaron, letrozole, Arimidex, etc.; antiandrogens: Flutamide RH-LH agonists/antagonists: zoladex, enantone, etc.; biological response regulators: interferons mainly inhibiting tumors via body immune functions; interleukin-2; thymosins; monoclonal antibodies: rituximab (MabThera); Cetuximab (C225); HERCEPTIN® (trastuzumab); Bevacizumab (Avastin); cell differentiation inducers such as Tretinoins; cell apoptosis inducers. The antibodies and compositions thereof as disclosed by the invention can be used in drug combinations with one or more of the aforesaid anti-tumor drugs.

In another aspect, the present invention provides a use of the anti-CD20 antibody or an antigen binding fragment thereof of the present invention or the conjugate of the present invention in the manufacture of a medicament for prophylaxis and/or treatment and/or diagnosis of cancer; the cancer includes a CD20 expressing cancer such as non-Hodgkin's lymphoma, B cell lymphoma, or chronic lymphocytic leukemia, and follicular lymphoma.

The present invention is further directed to a method for treating cancer. The method comprises the step of administering an effective amount of the anti-CD20 antibody or an antigen binding fragment thereof of the present invention to a subject in need thereof. The cancer includes a CD20 expressing cancer such as non-Hodgkin's lymphoma, B cell lymphoma, or chronic lymphocytic leukemia, and follicular lymphoma.

In a further aspect, the invention is directed to a method for treating autoimmune diseases. The method comprises the step of administering an effective amount of the anti-CD20 antibody or an antigen binding fragment thereof of the present invention to a subject in need thereof. Examples of autoimmune diseases suitable for treatment by the present method include immune-mediated thrombocytopenias, such as acute idiopathic thrombocytopenic purpurea and chronic idiopathic thrombocytopenic purpurea, dermatomyositis, Sydenham's chorea, lupus nephritis, rheumatic fever, polyglandular syndromes, Henoch-Schonlein purpura, post-streptococcal nephritis, erythema nodosum, Takayasu's arteritis, Addison's disease, erythema multiforme, polyarteritis nodosa, ankylosing spondylitis, Goodpasture's syndrome, thromboangiitis obliterans, primary biliary cirrhosis, Hashimoto's thyroiditis, thyrotoxicosis, chronic active hepatitis, polymyositis/dermatomyositis, polychondritis, pemphigus vulgaris, Wegener's granulomatosis, membranous nephropathy, amyotrophic lateral sclerosis, tabes dorsalis, polymyalgia, pernicious anemia, rapidly progressive glomerulonephritis and fibrosing alveolitis; inflammatory skin diseases including psoriasis and dermatitis (e.g. atopic dermatitis); systemic scleroderma and sclerosis; inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type 1 diabetes mellitus or insulin dependent diabetes mellitus); multiple sclerosis; Reynaud's syndrome; autoimmune thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious amenia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Bechet disease; giant cell arteritis; immune complex nephritis; IgA nephropathy; IgM polyneuropathies; immune thrombocytopenic purpura (ITP) or autoimmune thrombocytopenia etc.

The pharmaceutical composition of the present invention can be applied by systemic administration or local administration. Systemic administration includes oral, parenteral (such as intravenous, intramuscular, subcutaneous, or rectal), and other systemic routes of administration. In systemic administration, the active compound first reaches plasma and then distributes into target tissues.

Dosing of the composition can vary based on the extent of the cancer and each patient's individual response. For systemic administration, plasma concentrations of the active compound delivered can vary; but are generally $1\times10^{-10}$-$1\times10^{-4}$ moles/liter, and preferably $1\times10^{-8}$-$1\times10^{-5}$ moles/liter.

Those of skill in the art will recognize that a wide variety of delivery mechanisms are also suitable for the present invention.

The present invention is useful in treating a mammal subject, such as humans, horses, and dogs. The present invention is particularly useful in treating humans.

The invention is further illustrated by the following examples.

EXAMPLES

Example 1: Cloning of the Gene of Anti-CD20 Antibody MIL62

Experimental Materials:
Phusion polymerase, Taq DNA polymerase, restriction endonuclease, pGEM-T-easy vector, Pyrobest DNA polymerase, which are the products of NEB;
dNTP, DNA Marker standard, which are the products of TaKaRa;
DNA Recovery Kit, which is the product of Qiagen;
Trans2-Blue competent cell, which is the product of transgenbiotech;
Small-scale plasmid extraction kit (DP107-02), which is the product of Tiangen Biochemical;
Large-scale plasmid extraction kit (DP117), which is the product of Tiangen Biochemical; OPD, which is the product of Sigma;
FITC-labeled goat anti-human antibody, which is the product of Pierce;
Primer design was performed using the software from Biosun;
Primer synthesis (Genewiz), which was carried out by Genewiz Biotechnology (Beijing);

Gene sequencing was performed by Beijing Nuosai Genome Research Center Co., Ltd.

Experimental Methods and Results:
The genes of MIL62 antibody variable regions for both light- and heavy chain was synthesized by PCR and appropriate enzyme cleaving sites were introduced therein. The 5' and 3' termini of the light chain variable region of the antibody were introduced with ClaI and BsiwI sites; while the 5' and 3' termini of the heavy chain variable region of the antibody was introduced with EcoR I and Nhe I sites. The correct clones were sequenced, and the expression plasmid was assembled.

1.1 Primer Design

Primers were designed according to the principle of gene synthesis and using the computer-aided design software, taking into account the secondary structure of the respective primers, GC content and other related parameters. Ten (10) primers were designed for each gene numbered P1, P2, P3, P4, P5, P6, P7, P8, P9 and P10, which were used in gene synthesis.

1.2 Synthesis of the Full Gene

1) After synthesis, sterile water was used to dilute the primers using the following method:
a) The primers were centrifuged at 12,000 rpm for 2 min; the primers were then diluted to a concentration of 100 μM and stored at −20° C.
b) small amounts of primers P2 to P9 were mixed into a mixture with a final concentration of 10 μM as the working solution for future use
c) small amounts of primers P1 and P10 were mixed to reach a final concentration of 10 μM as the working solution of P1/P10.

2) Synthesis of the full gene, Pyrobest DNA polymerase was used, and the method was as follows:
a) 1 μL of the P2 to P9 primer mixture was taken as a template to prepare the following Overlap PCR system:

| | |
|---|---|
| P2 to P9 primer mixture | 1 μL |
| dNTP | 3 μL |
| 10 × Buffer | 5 μL |
| Pyrobest DNA polymerase | 0.3 μL |
| P1/P10 primers | 4 μL (primers are added later) |

The total volume was made up with sterile water to reach 50 μL.

b) Carried out the following reaction in the foregoing system:

| | | |
|---|---|---|
| 95° C. | 5 min | |
| 94° C. | 30 s | |
| 62° C. | 30 s | 7 cycles |
| 72° C. | 30 s | |
| 72° C. | 7 min | |

After completion of the reaction, the temperature was lowered to room temperature.

The P1/P10 primers were added and the following reaction was carried out:

| | | |
|---|---|---|
| 95° C. | 5 min | |
| 94° C. | 30 s | |
| 62° C. | 30 s | 25 cycles |
| 72° C. | 30 s | |
| 72° C. | 7 min | |

After completion of the reaction, the temperature was lowered to room temperature.

c) PCR products were isolated with 1 to 2% agarose gel electrophoresis. For the antibody heavy chain gene, a 440-bp size fragment was recovered. For the antibody light chain gene, a 400-bp size fragment was recovered.

d) Product recovery and addition of a tail (Pyrobest DNA polymerase cannot add 3' polyA tail to the PCR product, accordingly, the PCR product cannot be used directly with T vectors). The reaction system was as follows:

| Recovered fragment | 8.2 μL |
|---|---|
| 10 × Buffer | 1 μL |
| dNTP | 0.5 μL |
| Common Taq enzyme | 0.3 μL |

Reaction condition: 72° C. for 20 min. After completion of the reaction, the temperature was lowered to room temperature.

e) The product was linked with a tail to pGEM-TEasy vector:

| Tailed product | 4.2 μL |
|---|---|
| 2x ligation buffer | 5 μL |
| T vector | 0.5 μL |
| T4 DNA ligase | 0.3 μL |

The ligation reaction was carried out at room temperature for 2 h or 4° C. overnight. The ligation product was transformed into JM109 E. coli and spread on the LB agar medium containing 100 μg/mL ampicillin (final concentration). The obtained clones were then cultured in LB liquid medium containing 100 μg/mL of ampicillin (final concentration), and the plasmids was extracted with a plasmid extraction kit (Bertai Tektronix). The obtained plasmids were characterized by nucleic acid sequencing.

In the above steps, following Overlap PCR amplification and agarose gel electrophoresis analysis, the target bands in the specific size (410 base pairs and 440 base pairs) were obtained. Further, following the processes of product recovery, tail adding, cloning and other molecular biology technology, the target genes was successfully cloned into pGEM-TEasy vector. After sequencing, it was seen that the synthesized genes were consistent with the respective target sequences of interest.

Agarose electrophoresis results: VH was a target gene fragment of about 440 bp, Vκ was a target gene fragment of about 410 bp, which was respectively named MIL62/VH and
MIL62/Vκ.

Example 2: Construction of Antibody Eukaryotic Expression Vector

Experimental Materials:
Mabworks' proprietary dry powder medium manufactured by Hyclone was formulated and used in the cell cultures for host cell adaptation, cell line screening, and antibody preparation. Methionine sulfoximine (MSX) purchased from Sigma was added to the medium for cell line screening. In addition, the trypan blue dry powder purchased from Sigma was used to prepare a solution for cell counting.
Experimental Methods and Results:
pTGS-FRT-DHFR (Chinese patent ZL200510064335.0) was used as expression vector, in which hygromycin selection marker was removed, GS (glutamine synthetase) expression box was added via PshA1 and Xho1 restriction enzyme sites. The vector obtained by modification was named as GS vector.

The obtained MIL62 antibody light- and heavy chain variable region gene cloning vectors was then digested with the corresponding endonucleases (the light chain variable region gene was digested with ClaI and BsiwI, and the heavy chain variable region gene was digested with EcoR I and Nhe I), which are then linked with the vector digested with the same endonucleases. Through transformation and other conventional molecular biology techniques, the respective eukaryotic expression vectors were obtained. The specific steps were as follows:

a) The MIL62 light and heavy chain variable region genes of Example 1 were constructed into the pGEM-TEasy vector, and the obtained vectors were named MIL62/Vκ and MIL62/VH, respectively.

b) MIL62/Vκ was digested with ClaI and BsiwI, used to obtain the MIL62 light chain variable region gene.

c) 1 μg of GS vector was digested with ClaI and BsiwI. The resulting GS vector digested with ClaI and BsiwI was ligated with the antibody MIL62 light chain variable region gene (from step b) using T4 DNA ligase. The ligation product was transformed into XLI-blue E. coli and spread on LB agar medium containing 100 μg/mL ampicillin (final concentration). The obtained clones were then cultured in LB liquid medium containing 100 μg/mL of ampicillin (final concentration), and the plasmid was extracted with a plasmid extraction kit (Tiangen Biochemical Co., Ltd.). The extracted plasmid was then digested with ClaI and BsiwI and analyzed with 1% agarose gel electrophoresis to select a clone carrying the antibody MIL62 light chain variable region gene. The plasmid carrying the antibody MIL62 light chain variable region gene was named pTGS-MIL62Vκ.

d) The MIL62/VH was digested with EcoR I and Nhe I, to obtain the MIL62 heavy chain variable region gene.

e) 1 μg of pTGS-MIL62Vκ vector was digested with EcoR I and Nhe I. The resulting pTGS-MIL62Vκ vector digested with EcoR I and Nhe I was ligated with the antibody MIL62 heavy chain variable region gene (from step d) using T4 DNA ligase. The ligation product was transformed into XLI-blue E. coli and spread on LB agar medium containing 100 μg/mL ampicillin (final concentration). The obtained clones were cultured in LB liquid medium containing 100 μg/mL of ampicillin (final concentration), and the plasmid was extracted with a plasmid extraction kit (Tiangen Biochemical Co., Ltd.). The extracted plasmid was digested with EcoR I and Nhe I and analyzed with 1% agarose gel electrophoresis to select a clone carrying the antibody MIL62 heavy chain variable region gene.

The plasmid carrying the antibody MIL62 heavy chain variable region gene obtained on the basis of pTGS-MIL62Vκ was named MIL62.

Example 3: Development of the CHOK1-AF Cell Lines

The GDP-fucose transporter (GFT) SLC35C1 is known as a critically factor to regulate the fucosylation of glycans. With the absence of core fucose on Fc N-glycan of IgG1, the antibody has been shown to enhance the antibody dependent cytotoxicity (ADCC) effect, which is important to the function of MIL62 antibody.

CHO-K1 cells (CCL-61) purchased from ATCC were subjected to gene knockout so that the proteins expressed nearly or completely did not have fucosylation modification, and the obtained glycoengineered cell line was named as CHOK1-AF. Specific method comprised: modifying expression system by genetic engineering technique, in which site-specific knockout of key protein GFT for fucosylation modification route was carried out in host cell CHO-K1 for antibody expression to effectively reduce fucose modification level of antibody. This method could simultaneously block typical fucosylation mechanism and compensation mechanism, so as to achieve complete removal of fucosylation.

Specific technical route was shown in FIG. 1, in which by using zinc-finger nuclease technique, two GFT zinc-finger nuclease sequences were designed for GFT gene SLC35c1 sequence (GenBank: BAE16173.1) and used to bind double-stranded DNA of target genes. Expression vector pCDNA3.1-G1F1 and pCDNA3.1-G2F2 were correspondingly constructed, and co-transfected into CHO-K1 cells by electrotransfection technique. The transfected cells were static cultivated on 6-well plate for 24 h and then transferred in 125 mL shake flask and cultured under shaking to perform passage and amplification in the shake flask. By using the specific affinity of saccharide-binding agglutinin LCA (Lens culinaris agglutinin) to protein fucosyl, the co-transfected cells were stained with biotin-LCA, negative separation was carried out by using anti-biotin microBeads and MACs LD column in combination, clonal culture was further performed, and fucose knockout level of clonal cells was determined by flow cytometry technique; and clone 1G7 without fucosylation modification was obtained via multi-turns of negative separation and clonal culture.

Figure 2:
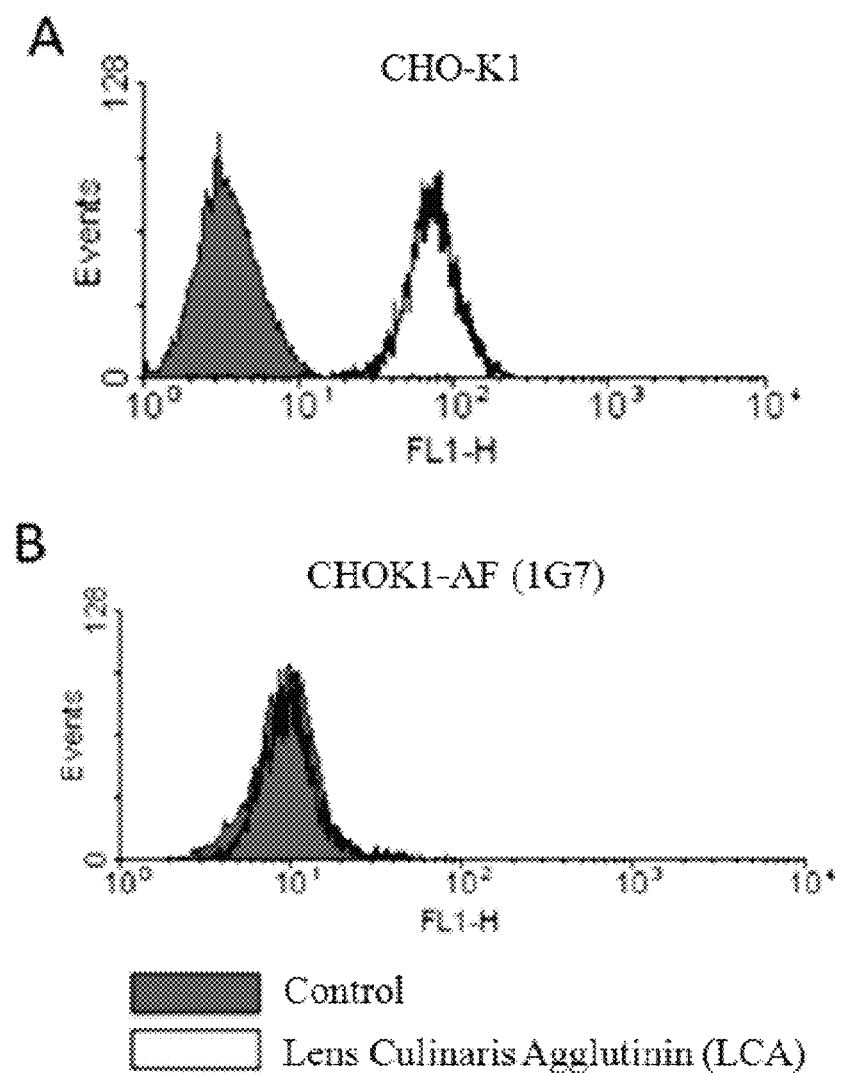
FIG. 2 shows the fucose expression level of CHO-K1 cells (A) and CHOK1-AF cells (B) determined by FACS.

FIGS. 2A and 2B show the fucose expression level of CHO-K1 cells (A) and CHOK1-AF cells (B). The dark color-filled peak refers to the control cells which do not express fucose. The black line peak represents the fucose expression level of CHO-K1 (A) or CHOK1-AF cells (B) determined by FCAS using Lens culinaris agglutinin (LCA) reagent, which has high specific binding affinity to the fucose unit. The results show that CHO-K1 cells express high level of fucose and CHOK1-AF cells do not express the fucose.

The CHOK1-AF cell was deposited in China General Microbiological Culture Collection Center (No. 1 West Beichen Road, Chaoyang District, Beijing 100101, China) on Jun. 14, 2017, with a deposit number of CGMCC No. 14287.

The total RNA of clone 1G7 without fucosylation modification was extracted, after reverse transcription, the gene encoding GDP transport protein was taken and sequenced to confirm that this gene was mutated successfully, and could not be normally expressed.

Example 4. Preparation of Specific Culture Media

The culture media were prepared according to Table 1-1, 1-2, 1-3. The media were sterile-filtered through a 0.22-μm membrane, and saved for future cell culture.

TABLE 1-1

Seed medium

| No. | Component | Content |
|---|---|---|
| 1 | Injection water (25 ± 5 C. °) | 0.9 L |
| 2 | Pluronic F-68 | 1.0 g/L |
| 3 | Glucose | 8.8 g/L |
| 4 | Medium dry powder Maxgrow 202 | 7.44 g/L |
| 5 | Sodium bicarbonate | 1.98 g/L |

TABLE 1-1-continued

Seed medium

| No. | Component | Content |
|---|---|---|
| 6 | Sodium chloride | 3.47 g/L |
| 7 | 1M HEPES | 15 mL/L |
| 8 | 5M HCl or 5M NaOH | pH is adjusted to 7.0 ± 0.1 |
|  | Reach final volume of 1 L |  |

TABLE 1-2

Production medium

| No. | Component | Content |
|---|---|---|
| 1 | Injection water (25 ± 5 C. °) | 0.8 L |
| 2 | Sodium hydroxide | 0.8 g/L |
| 3 | Medium dry powder Maxpro 302 | 11.5 g/L |
| 4 | 1 g/L vitamin B12 stock solution | 1-2 mL/L |
| 5 | 10 g/L Ferrous sulfate stock solution | 0.4-0.6 mL/L |
| 6 | Sodium dihydrogen phosphate monohydrate | 0.35 g/L |
| 7 | Glucose (monohydrate) | 8.8 g/L |
| 8 | L-cysteine hydrochloride monohydrate | 0.3-0.375 g/L |
| 9 | Pluronic F-68 | 1 g/L |
| 11 | Sodium chloride | 1.55 g/L |
| 12 | 5M HCl | 5.6 mL/L |
| 13 | Sodium bicarbonate | 1.22 g/L |
| 14 | 1M HEPES | 7.5 mL/L |
| 15 | 5M HCl or 5M NaOH | pH is adjusted to 7.0 ± 0.1 |
|  | Reach final volume of 1 L |  |

TABLE 1-3

Feed medium

| No. | Component | Content |
|---|---|---|
| 1 | Injection water (25 ± 5 C. °) | 0.8 L |
| 2 | 5M sodium hydroxide | 7.325 mL |
| 3 | Anhydrous disodium hydrogen phosphate | 3.09 g/L |
| 4 | Fed-batch medium dry powder Maxfeed 402 | 39.03 g/L |
| 5 | 50 g/L L-tyrosine disodium dihydrate | 23.8 mL |
| 6 | 50 g/L L-cysteine hydrochloride monohydrate | 23.2 mL |
| 7 | Glucose | 50.0 g/L |
| 8 | 1.75 g/L vitamin B12 | 0.3 mL |
| 9 | 5 g/L Ferrous sulfate heptahydrate | 0.3 mL |
| 10 | Pluronic F-68 | 0.3 g |
| 11 | Sodium chloride | 0.24 g |
| 12 | Sodium bicarbonate | 0.366 g |
| 13 | 5M HCl or 5M NaOH | pH is adjusted to 7.0 ± 0.1 |
|  | Reach final volume of 1 L |  |

Example 5. Preparation of MIL62 Antibody

The eukaryotic expression vector of MIL62 antibody obtained in Example 2 was transfected to the glycoengineered CHOK1-AF host cell (obtained by screening in Example 3) by way of electrical transformation. 75 μM MSX was added to the seed culture medium, the cells were cultured at 37° C. in a $CO_2$ incubator for 2 to 4 weeks. The cells that were viable in the selection medium were then selected, and detected by ELISA to obtain the cells capable of expressing the antibody. Subclone screening was performed by limiting dilution method, and after 6-8 weeks of culture and screening, the monoclonal cell lines capable of efficiently expressing MIL62 antibody were obtained.

The cell line was amplified by multi-step culture in culture media with a seeding density of $0.5 \times 10^6$ cells/mL.

The cells were passaged at 3-day interval, until the cells were in a sufficient amount, and then the cells were transferred to a production medium (1:1 ratio of production medium:seed medium) to start fed-batch culture. The culture was about 12 to 14 days. During the fed-batch, the feed medium in an amount of 10% by volume was added on the 3rd, 6th and 9th day of culture. Finally, the supernatant was harvested after the culture was finished, and the supernatant was purified.

The isolation and purification of MIL62 antibody were carried out using AKTA (GE). The eluate through the protein A affinity column (MabSelect SuRe) within the pH range of 3.4 to 3.6 (monitored at 280 nm) was collected, and then adjusted to pH 8.0; which was next loaded to an anion exchange column (Q-Sepharose FF), monitored at 280 nm and the samples were collected. The pH of the collected solution was next adjusted to 5.5, which was then loaded to a cation exchange column (Poros), and the samples were collected. Ultrafiltration was carried out next to obtain the MIL62 antibody. The specific process was shown in FIG. 6.

The antibody MIL62 prepared was then used in the following examples.

Example 6. MIL62 Antibody N-Glycan Analysis

Experimental Method:

MIL62 antibody, 500 μg, was desalted in a 10-kD ultrafiltration tube, then added with 10 μL of G7 enzyme digestion buffer (New England BioLabs, Product#P0705L), 3 μL of PNGase F, and ultra-pure water to reach 100 μL. The tube was mixed well and then sealed with a sealing film, placed in a 37° C. water bath for incubation overnight. The digested sample was added with 300 μL of pre-cooled ethanol, mixed well and incubated for 30 min, centrifuged at 12,000 rpm for 5 min, and the resulting supernatant was concentrated and dried. DMSO and acetic acid were mixed according to the ratio of 350 μL:150 μL. 5 mg of 2-AB and 6 mg of sodium cyanoborohydride were added to dissolve in 100 μL of the mixture of DMSO and acetic acid. 10 μL of the resulting mixture was placed in an oven at 65° C. for 3 h; subsequently, 200 μL of 80% mixture of acetonitrile and water was added, centrifuged for 2 min, and the supernatant was obtained.

HILIC-UPLC Analysis:

Column: WATERS Acquity UPLC BEH Amide 1.7 μm, 2.1×50 mm column;

Column temperature: 40° C.;

Excitation wavelength: λex=330 nm; λem=420 nm;

Injection volume: 10 μL;

The column was equilibrated with 20% mobile phase A (100 mM ammonium formate, pH 4.5) and 80% mobile phase B (100% acetonitrile). After injection, the proportion of phase A was further increased to 40% after 36 min.

Figure 4:
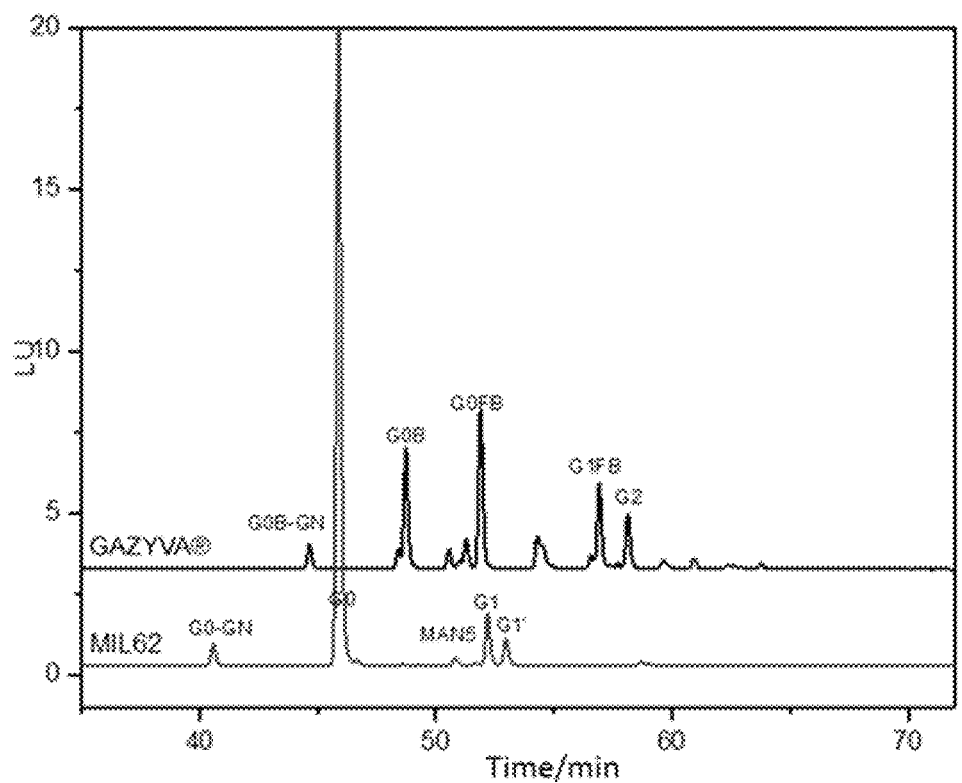
FIG. 4 shows the distribution of N-glycans that were enzymatically released from MIL62 and GAZYVA®.

Experimental Results:

The hydrophilic interaction liquid chromatography (HILIC) HPLC analysis of the N-glycans that were enzymatic released from monoclonal antibodies MIL62 and GAZYVA® is displayed in FIG. 4. The identities of the N-glycans were determined according to their molecular mass, peak retention pattern in comparison with the standard reference spectra of different sugar forms. Their distribution ratios (percentages) were determined according to their peak area divided by the total area of all peaks observed on the chromatograms and the results are displayed in Table 2 and Table 3, for MIL62 and GAZYVA®, respectively. The structures of the main N-glycans that were enzymatically released from MIL62 and GAZYVA® are shown in FIG. 3.

TABLE 2

The identities and distribution ratios of the N-glycans released from MIL62 antibody

| N-glycans | G0-GN | G0 | G0F | Man5 | G1 | G1' | G2 | Other |
|---|---|---|---|---|---|---|---|---|
| Ratios (%) | 2.03 | 74.84 | 0.43 | 1.06 | 11.77 | 7.24 | 1.33 | 1.3 |

TABLE 3

The identities and distribution ratios of the N-glycans released from GAZYVA ® antibody

| N-Glycan | G0B-GN | G0F B-GN | G0B | Man5 | G1B-GN | G0FB | G1 FB-GN | G1B | G1FB | G2 | G2F | Other |
|---|---|---|---|---|---|---|---|---|---|---|---|---|
| Ratios (%) | 3.75 | 2.72 | 18.29 | 2.92 | 4.71 | 24.18 | 5.48 | 4.01 | 13.61 | 8.62 | 2.04 | 9.67 |

As shown in Tables 2 and 3, two distinctive features can be drawn for the N-glycans released from MIL62 and GAZYVA®. (1) The content of the N-glycans containing the core fucosylation is extremely low for MIL62, i.e. 0.43% for the example batch of MIL62. However, the content is much higher for GAZYVA®, i.e 48.03% for the example batch of GAZYVA®. It is reasonable to deduce that GAZYVA® batch productions would never achieve the core fucosylation level lower than 30% because of the following reasons. First, as a critical quality attribute of the GAZYVA® therapeutic product, the core-fucosylation level should be controlled in a certain range. Second, mechanistically, inhibition of the fucosylation process in the CHO cells by introducing bisecting GlcNAc to the N-glycans as an indirect method would not reduce the core fucosylation to a very low level. This conclusion can be drawn based on the afucosylation ratios of the same glycotype pairs being not low at all, such as G0B/G0FB (18.29/24.18), G1B/G1FB (4.01/13.61) etc., as shown in Table 3. In addition, the inserting of bisecting GlcNAc is not complete as there were about 24% of the total N-glycans produced without the bisecting GlcNAc. (2) The N-glycans released from MIL62 have none of the bisecting-GlcNAc containing species; on the contrary, the bisecting-GlcNAc containing N-glycans account for more than 76% for GAZYVA®.

Example 7. MIL62 Antibody Protein Molecular Mass Analysis

Deglycosylation of MIL62 sample: MIL62 antibody 500 μg was desalted in a 10-kD ultrafiltration tube; it was added with 10 μL of G7 digestion buffer, 3 μL of PNGase F, and ultra-pure water to reach 100 μL, mixed well and then sealed with a sealing film, placed in a 37° C. water bath for incubation overnight.

LC/MS analysis: MIL62 or deglycosylated samples were diluted to 2.5 mg/mL and the samples were further desalted using a PLRP-S column: 95% mobile phase A (0.1% FA water), 5% mobile phase B (0.1% FA acetonitrile), at 10 min, the gradient was 95% of the mobile phase B, which was maintained for 10 min; the samples were desalted using a reverse column, and analyzed with TripleTOF 4600 (AB Sciex) mass spectrometry. Data were further subjected to deconvolution analysis with Analyst TF1.6.

Figure 5A:
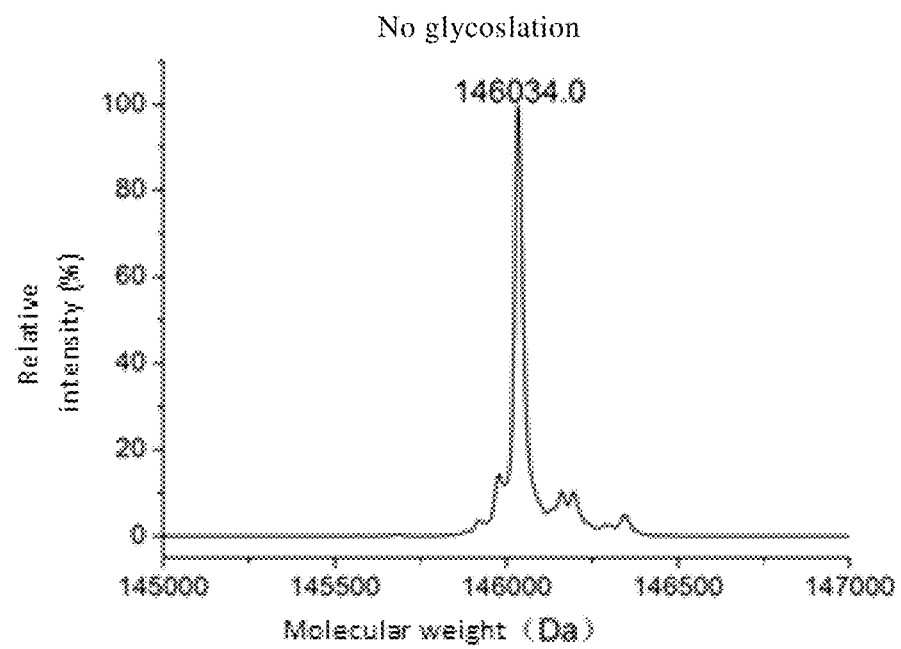
FIGS. 5A and 5B show the mass spectra of the complete MIL62 protein with or without glycosylation.
Figure 5B:
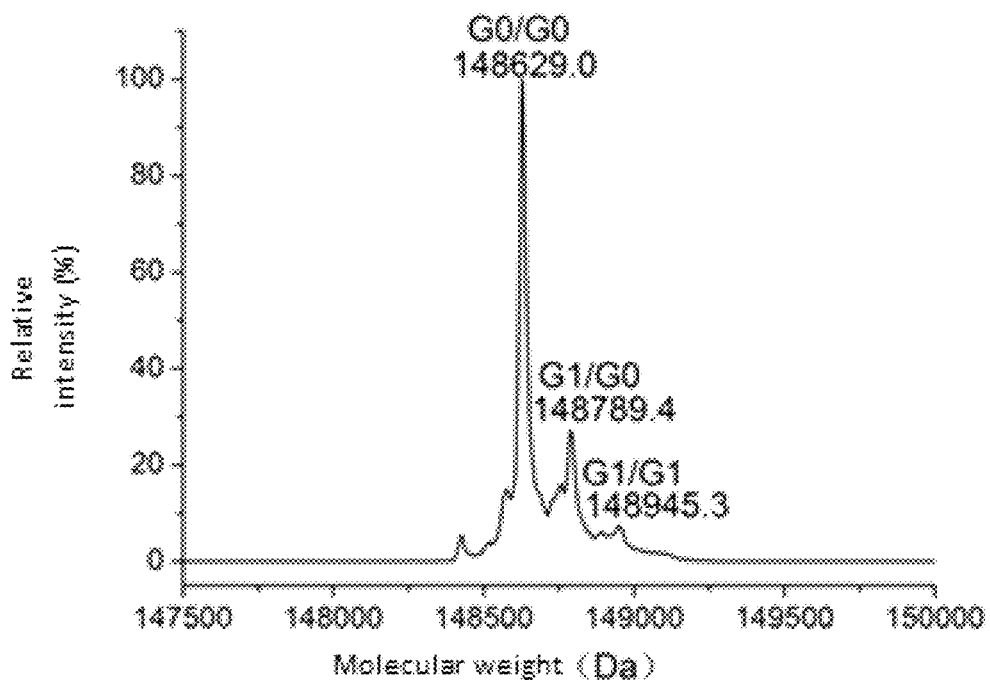

Experimental results: The mass spectra of the complete protein with or without glycosylation are shown in FIGS. 5A and 5B.

Example 8. ADCC Activity

Target cells Daudi (purchased from ATCC, CCL-213), effector cells NK92MI-CD16a (purchased from Huabo Bio) were centrifuged at 1200 rpm for 4 min, and the supernatants were discarded. ADCC experimental culture medium was used to re-suspend cells, then centrifuged at 1200 rpm for 4 min, and supernatants were discarded. ADCC experimental culture medium was used to re-suspend cells, and the cell viability was ≥90% according to cell counting. Daudi cell density was adjusted to $2.5 \times 10^5$/ml. NK92MI-CD16a cell density was adjusted to $1.25 \times 10^6$/ml.

Antibodies of different concentrations were separately added to achieve final concentrations of 0.000001 ng/ml, 0.00001 ng/ml, 0.0001 ng/ml, 0.001 ng/mL, 0.01m/mL, 0.1 ng/mL, 1 ng/mL, 10 ng/mL, 100 ng/mL, and 1000 ng/ml, respectively, then the effector cells and target cells (effector-target ratio was 10:1) were added, incubated at 37° C. for 4 h. LDH developing solution was added at 100 μL/well, and the plate was placed in a dark place at room temperature for 20 min. Determination was carried out using a MD SpectraMax i3.

With regard to the target cell of Raji (purchased from the Cell Bank of Chinese Academy of Sciences, TCHu44), the ADCC testing method was performed as same as that for Daudi.

Calculation of Killing Rate:
Background group: culture medium group
Minimum release group: target cell group
Maximum release group: target cell+lysis solution group
Experimental groups: target cell+effector cell Killing rate (%) or inhibition (%)=[(experimental group−minimum release group)/(maximum release group−minimum release group)]×100

Figure 6:
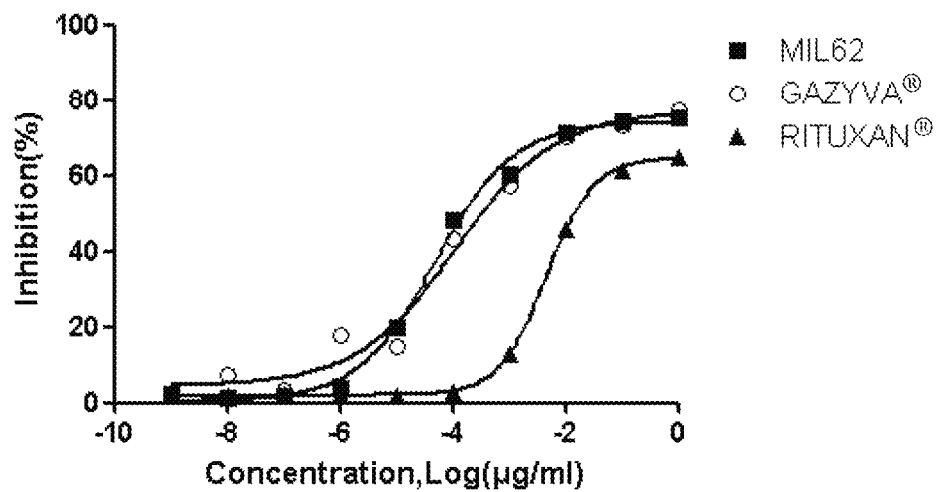
FIG. 6 shows the ADCC activities of MIL62, GAZYVA®, and RITUXAN® to target cells Daudi.
Figure 7:
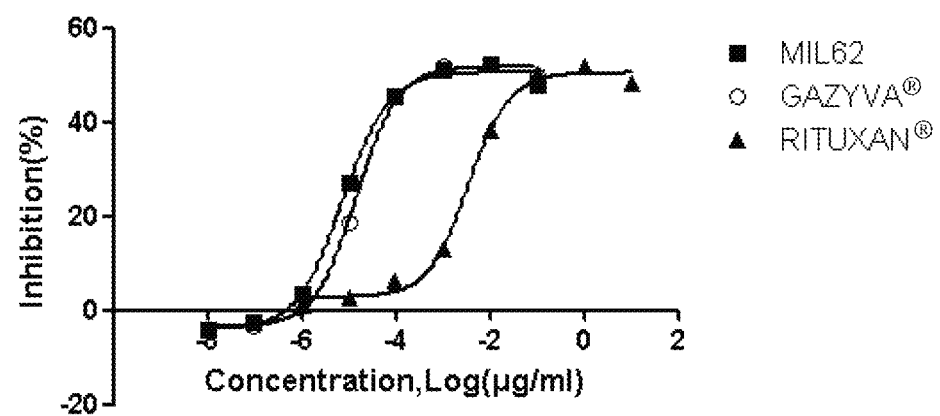
FIG. 7 shows the ADCC activities of MIL62, GAZYVA®, and RITUXAN® to target cells Raji.

Experimental Results:
FIGS. 6 and 7 show the results that the ADCC activities of MIL62 to target cells Daudi and Raji were significantly superior to RITUXAN® and GAZYVA®, and the cell killing effects were dose dependent.

Example 9. FcγRIIIa Binding Activity

High protein binding Costar 96-well plates were coated with anti-His antibody (Genscript, A00186) (1 μg/ml, 100 μl/well) in a coating buffer (0.05 M sodium carbonate buffer, pH 9.6) overnight at 4° C. The wells were washed twice with PBS/0.05% Tween 20 (pH 7.4). The plates were blocked with 5% Non-Fat Milk Powder/PBS (pH 7.4) for 1.5 hours at 37° C. Plates were washed and FcγRIIIa (Sino Biological Inc, 10389-H08C1) (1m/ml, 100 μl/well) in PBS/0.05% Tween 20, pH 7.4 (assay buffer) was added to the plates. Antibodies were pre-incubated with goat F(ab')2 anti-human-κ antibody (Sigma) at a 1:2 (w/w) ratio in assay buffer for 1 h to form complex to increase binding avidity. The complexed IgG (for MIL62 and GAZYVA® 0.78-50000 ng/ml in 3-fold serial dilution in duplicate; for RITUXAN®, 22.86-5000 ng/ml in 3.5-fold serial dilution in duplicate) was added to the plates. After a 2 h incubation, plates were washed and bound IgG was detected by adding horseradish peroxidase (HRP) labeled goat F(ab')2 anti-human IgG F(ab')2 (Sigma). After a final 1 hour incubation, plates were washed and the substrate 3,3',5,5'-tetramethyl benzidine (TMB) (InnoReagents) was added. The reaction was stopped by adding 1 M phosphoric acid, and the OD was measured at 450 nm using a microplate reader Spectra MAX 13 (Molecular Devices).

Figure 8:
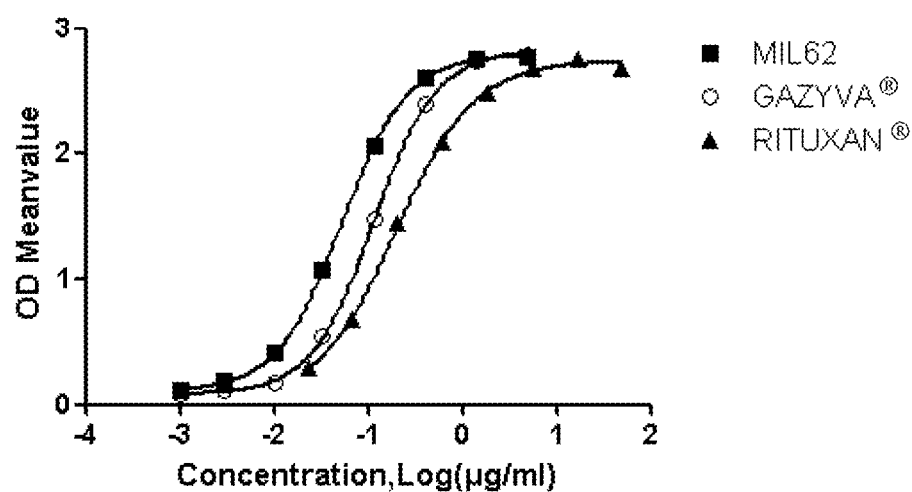
FIG. 8 shows the EC50 of FcγRIIIa binding activity for MIL62, GAZYVA®, and RITUXAN®, respectively.

FIG. 8 shows that the EC50 of FcγRIIIa binding activity were 0.055 μg/mL, 0.113 μg/mL, and 0.194 μg/mL for MIL62, GAZYVA®, and RITUXAN®, respectively. These results indicate an affinity ranking of MIL62>GAZYVA®>RITUXAN® for FcγRIIIa(V158).

Example 10. Direct Cell-Killing Activity

Human B lymphocyte SU-DHL-4 cells (purchased from ATCC) in logarithmic phase were counted, viability rate>90%, regulated to have cell density of $4 \times 10^5$ cells/ml, mixed evenly, and inoculated in an amount of 50 μL/well on a cell culture plate. Antibody MIL62, GAZYVA®, RITUXAN® were diluted and added in an amount of 50 μL/well to 96-well culture plate on which cells were spread in advance. For each antibody, 9 concentrations: 5m/mL, 1.25 μg/mL, 0.313m/mL, 0.078m/mL, 0.020m/mL, 0.005 μg/mL, 0.0013 μg/mL, 0.0003m/mL, 0.0001m/mL, were set. Replicated wells were set for each concentration. In addition, a drug-free control group and a cell culture medium blank control group were set. The culture plate was placed in a cell incubator and incubated for 48 h, then 10 μl of CCK-8 solution was added to each well, the culture plate was placed in the incubator and incubated for 4 h. $OD_{450}$ values were determined with microplate reader Spectra MAX 13 (Molecular Devices). Inhibition percentages of drugs to cells were calculated by the following formula: inhibition percentage=(1−(drug group $OD_{450}$−blank group $OD_{450}$)/(control group $OD_{450}$−blank group $OD_{450}$))*100%.

Figure 9:
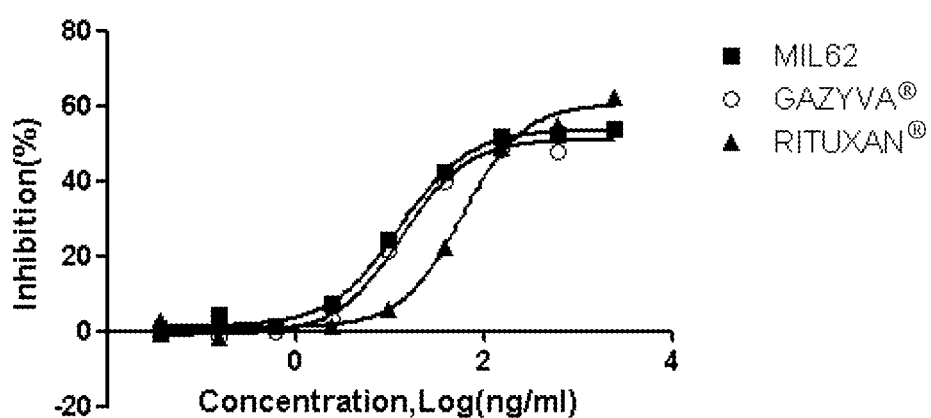
FIG. 9 shows the growth inhibition curve of SU-DHL-4 cells by MIL62, GAZYVA®, and RITUXAN®.

As shown in FIG. 9, the growth inhibition percentage of MIL62 on SU-DHL-4 cells were very close to that of GAZYVA®, but significantly higher than that of RITUXAN®, and the inhibition effects were also depended on antibody dosage.

Example 11. CDC Activity

Target cells Daudi were centrifuged at 1200 rpm for 4 min, and supernatant was discarded. The cells were re-suspended with 10% FBS culture medium, counted, cell viability should be ≥90%. Cell density of BT474 cells was adjusted to $1 \times 10^6$/ml, 50 μl per well. Antibodies of different concentrations were separately added, MIL62 and GAZYVA® final concentrations were 1200 μg/mL, 300 μg/mL, 75 μg/mL, 18.75 μg/mL, 4.69 μg/mL, 1.17 μg/mL, 0.30 μg/mL, 0.075 μg/mL, 0.019 μg/mL, and 0.0047 μg/ml, respectively. 50 μl of human complement (1:4 dilution) was added, incubated at 37° C. for 2 h, added with CCK-8 developing solution, 15 μL/well, the culture plate was placed in the incubator and incubated for 4 h. $OD_{450}$ values were determined with microplate reader Spectra MAX 13 (Molecular Devices). Inhibition rates of drugs to cells were calculated by the following formula: inhibition rate=(1−(drug group $OD_{450}$−blank group $OD_{450}$)/(control group $OD_{450}$−blank group $OD_{450}$))*100%.

Figure 10:
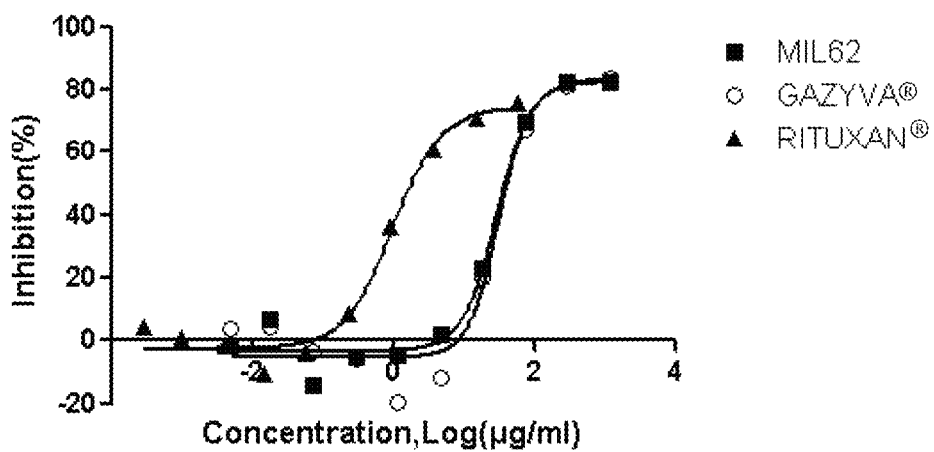
FIG. 10 shows the CDC activity on target Daudi cells by MIL62, GAZYVA®, and RITUXAN®.

As shown in FIG. 10, MIL62 and GAZYVA® had similar CDC activity to Daudi cells, but had lower CDC activity than that of RITUXAN®.

Example 12. Summary of the Bioactivity Test Results for MIL62®, GAZYVA®, and RITUXAN®

The bioactivity results from Examples 8-11 are summarized in Table 4 below.

TABLE 4

Bioactivity comparison with 3 anti-CD20 antibodies.

| Bioactivity Tests | Antibody | EC50 (µg/ml) | Relative Bioactivity (%) |
|---|---|---|---|
| ADCC Target cell: Daudi | MIL62 | 4.88E-5 | 100 |
| | GAZYVA | 11.09E-5 | 44.0 |
| | RITUXAN | 453E-5 | 1.1 |
| ADCC Target cell: Raji | MIL62 | 0.738E-5 | 100 |
| | GAZYVA | 1.427E-5 | 51.7 |
| | RITUXAN | 34.47E-5 | 2.1 |
| Binding ELISA FcγRIIIa(V158) | MIL62 | 0.052 | 100.0 |
| | GAZYVA | 0.113 | 46.0 |
| | RITUXAN | 0.194 | 26.8 |
| Direct cell killing Target cell: Su-DHL-4 | MIL62 | 0.012 | 100.0 |
| | GAZYVA | 0.013 | 92.3 |
| | RITUXAN | 0.058 | 20.7 |
| CDC Target cell: Daudi | MIL62 | 29.57 | 100.0 |
| | GAZYVA | 31.51 | 93.8 |
| | RITUXAN | 0.98 | 3017.3 |

Table 4 shows that the antibody dependent cell-mediated cytotoxicity (ADCC) of MIL62 is about 2 times stronger than that of GAZYVA® and 50 to 100 times stronger than that of RITUXAN®. MIL62 has similar direct cell killing activity targeting Su-DHL-4 cells as GAZYVA® and both are about 5 times stronger than that of RITUXAN®. The complement dependent cytotoxicity (CDC) of MIL62 is similar to that of GAZYVA®, but both are about 30 times less active than that of RITUXAN®.

Figure 11:
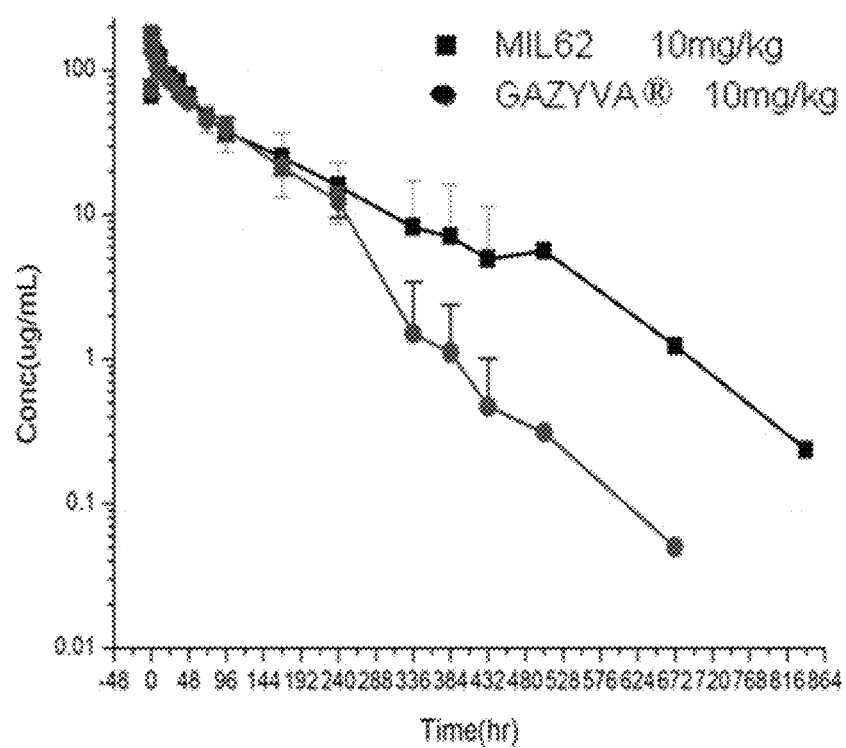
FIG. 11 shows the drug-time course in serum following the single i.v. dose of the MIL62/GAZYVA®.

Example 13. Preliminary Pharmacokinetic Test of MIL62 Versus GAZYVA® in Cynomolgus Monkeys Six cynomolgus monkeys were randomly divided into 2 groups (3 monkeys per group, 1 female and two males). Each monkey was single dosed by intravenous infusion with 10 mg/kg of MIL62 and reference drug (GAZYVA®), respectively. The blood samples were collected from the monkeys at 0 min, 15 min, 30 min (infusion end), 2 h, 4 h, 8 h, 12 h, 24 h, 36 h, 2 d, 3 d, 4 d, 7 d, 10 d, 14 d, 16 d, 18 d, 21 d, 28 d and 35 d time points. The concentration of drug in serum samples was quantitatively detected by enzyme-linked immunosorbent assay (ELISA), its lower limit of quantitation (LLOQ) is 100 ng/mL. The drug-time course in serum following the single i.v. dose of the antibody is shown in FIG. 11. Y-axis is the MIL62/GAZYVA® concentration in serum as determined by ELISA; X-axis is time after dose of the antibody. The calculated average PK parameters are shown in Table 5.

TABLE 5

Average pharmacokinetic parameters of MIL62 and GAZYVA ® after single intravenous infusion of cynomolgus monkeys (Mean ± SD, n = 3)

| Parameters | Unit | MIL62 (n = 3) | GAZYVA ® (n = 3) |
|---|---|---|---|
| $t_{1/2}$ | hr | 80.21 ± 6.89* | 41.92 ± 16.31* |
| $T_{max}$ | hr | 1 ± 0.87 | 0.5 ± 0 |
| $C_{max}$ | ug/mL | 174.8 ± 34.67 | 165.23 ± 27.94 |
| $AUC_{(0-t)}$ | hr*ug/mL | 14083.95 ± 4413.59 | 10803.89 ± 1065.68 |
| $AUC_{(0-inf)}$ | hr*ug/mL | 17838.92 ± 7914 | 10808 ± 1065.63 |
| $AUC_{(t-inf)\%}$ | % | 15.7 ± 22.83 | 0.04 ± 0.01 |
| $V_d$ | mL/kg | 231.22 ± 131.98 | 166.11 ± 52.86 |
| CL | mL/hr/kg | 1.96 ± 0.98 | 2.79 ± 0.27 |
| MRT | hr | 139.75 ± 53.04 | 88.29 ± 9.81 |

Table 5 shows that the end phase half-life t1/2 were 80.21±6.89 hr and 41.92±16.31 hr for MIL62 and GAZYVA®, respectively. The peak reaching time $T_{max}$ were 1±0.87 hr and 0.5±0 hr; the peak concentration $C_{max}$ were 174.8±34.67m/mL and 165.23±27.94 µg/mL; the $AUC_{(0-t)}$ were 4083.95±4413.59 hr·m/mL and 10803.89±1065.68 hr·m/mL for respective MIL62 and GAZYVA®. The results showed that the end phase half-life t1/2 of MIL62 was longer than reference drug of GAZYVA®. However, excluding the end phase t1/2, there is no significant statistic meaningful difference for other PK parameters between the two antibody drugs.

It is to be understood that the foregoing describes preferred embodiments of the present invention and that modifications may be made therein without departing from the scope of the present invention as set forth in the claims.

What is claimed is:

1. Humanized anti-CD20 antibodies comprising:
   a light chain comprising the amino acid sequence of SEQ ID NO: 1,
   a heavy chain comprising the amino acid sequence of SEQ ID NO: 2, and
   N-glycans that are attached to the Fc region of the antibody,
   wherein the N-glycans are not bisected by N-acetylglucosamine, and the N-Glycans consist of G0-GN, G0, G0F, Man5, G1, G1" and G2.

2. A pharmaceutical composition comprising antibodies of claim 1 and a pharmaceutically acceptable carrier, diluent and/or adjuvant.

* * * * *